(12) United States Patent
Cavitt et al.

(10) Patent No.: US 8,904,583 B1
(45) Date of Patent: Dec. 9, 2014

(54) PEDIATRIC CATHETERIZATION COLLAR

(76) Inventors: Robert Cavitt, South Lyon, MI (US);
Dianne Cavitt, South Lyon, MI (US)

(*) Notice: Subject to any disclaimer, the term of this patent is extended or adjusted under 35 U.S.C. 154(b) by 247 days.

(21) Appl. No.: 13/453,935

(22) Filed: Apr. 23, 2012

Related U.S. Application Data

(60) Provisional application No. 61/477,686, filed on Apr. 21, 2011.

(51) Int. Cl.
*A61G 13/12* (2006.01)

(52) U.S. Cl.
USPC .................................................. 5/621; 5/622

(58) Field of Classification Search
USPC ....................................... 5/621–622, 636–637
See application file for complete search history.

(56) References Cited

U.S. PATENT DOCUMENTS 6,557,195 B2 * 5/2003 Dinkler ............................ 5/601

* cited by examiner

*Primary Examiner* — Fredrick Conley
(74) *Attorney, Agent, or Firm* — Vincent Re PLLC

(57) ABSTRACT

A pediatric catheterization collar for enlarging the working surface of a medical treatment bed to enable medical personnel to treat a child upon an adult-sized treatment bed. The collar having a U-shaped profile that mounts atop the cantilevered mattress support plate of the bed. The collar surrounding one end of the mattress and having a table top that is substantially coplanar with the top surface of the mattress.

7 Claims, 2 Drawing Sheets

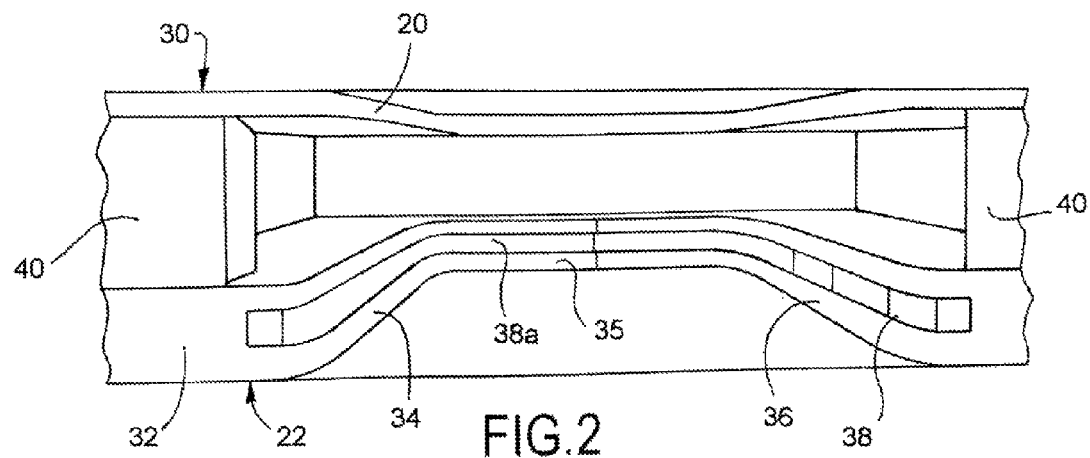
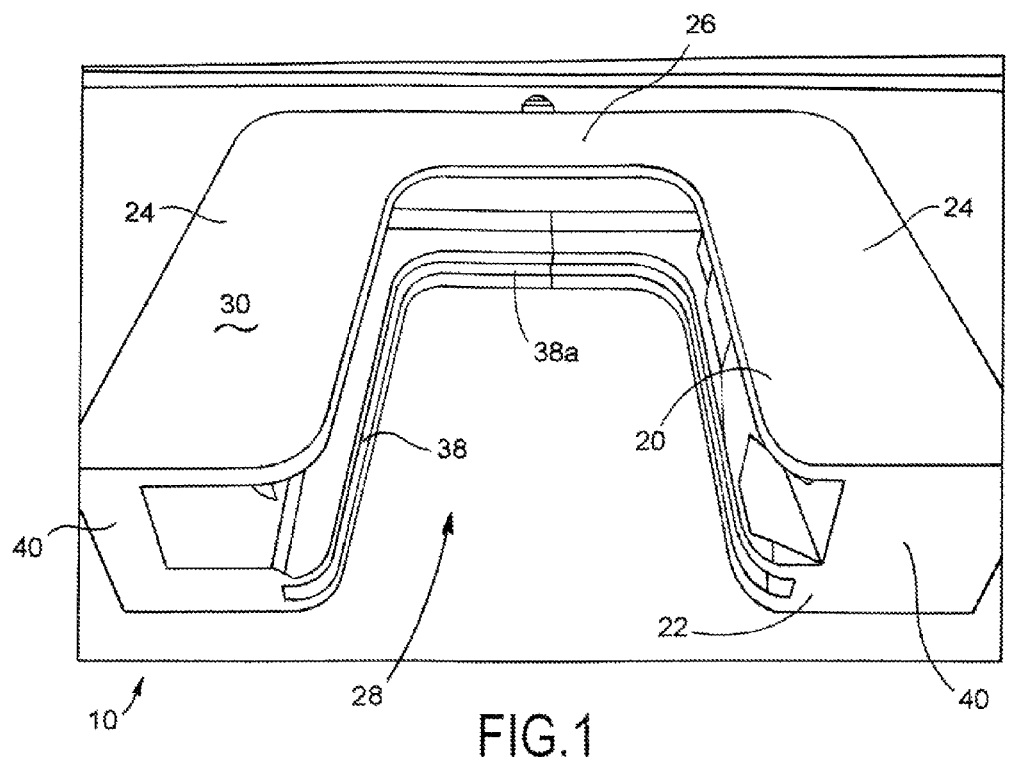

PEDIATRIC CATHETERIZATION COLLAR

CROSS-REFERENCE TO RELATED APPLICATIONS

This application claims priority of United States Provisional Patent Application filed Apr. 21, 2011 having Ser. No. 61/477,686.

FIELD OF THE INVENTION

The present invention relates to an accessory for positioning a pediatric patient during surgical and/or X-ray procedures and, more particularly, to a table-mounted collar for supporting a patient's arms above his head to permit catheterization for a fluoroscopic procedure or other medical examination or procedure without interference from the patient's arms.

BACKGROUND AND SUMMARY OF THE INVENTION

Catheterization is a relatively non-invasive medical procedure where a flexible hollow tube is inserted into a vein or artery of a patient to allow doctors access into a patient for treatment and/or diagnosis of an ailment. Children, and babies in particular, that require catheterization present a particular challenge to the procedure as their small bodies are often placed on adult-sized treatment beds. To ensure their arms remain out of the way during the procedure these patients are catheterized with their arms overhead. These beds are not sized for these patients and the medical personnel must oftentimes position the patient using an ad-hoc support of towels and medical tape.

Accordingly, it is an advantage of the present invention to provide a device that is removably mounted to a conventional adult-sized treatment bed that supports the overhead arms of a smaller patient, without interfering with the surgical or imaging procedure.

It is a further advantage of the invention to provide an arm positioning collar that is of simple construction that may be provided as an accessory to provide a simple solution for positioning smaller patients during catheterization and catheter-based procedures.

The foregoing advantages have been realized by providing a unique support collar having a recessed slot for mating to a treatment bed. The platform has a flat upper surface that lies in-plane with the top surface of the bed's mattress allowing placement of the patient's arm thereon without the risk of superabduction of the limbs or otherwise stressing the patient's upper body.

These and other objects, features and advantages of the present invention will become apparent from the following description when viewed in accordance with the accompanying drawings.

BRIEF DESCRIPTION OF THE DRAWINGS

The description refers to the accompanying drawings in which like reference characters refer to like parts throughout the several views, and in which:

FIG. 1 is a top perspective view of the present invention;
FIG. 2 is a partial front view of the present invention showing the spaced table and mounting structure slot.

DETAILED DESCRIPTION OF THE INVENTION

Figure 3:
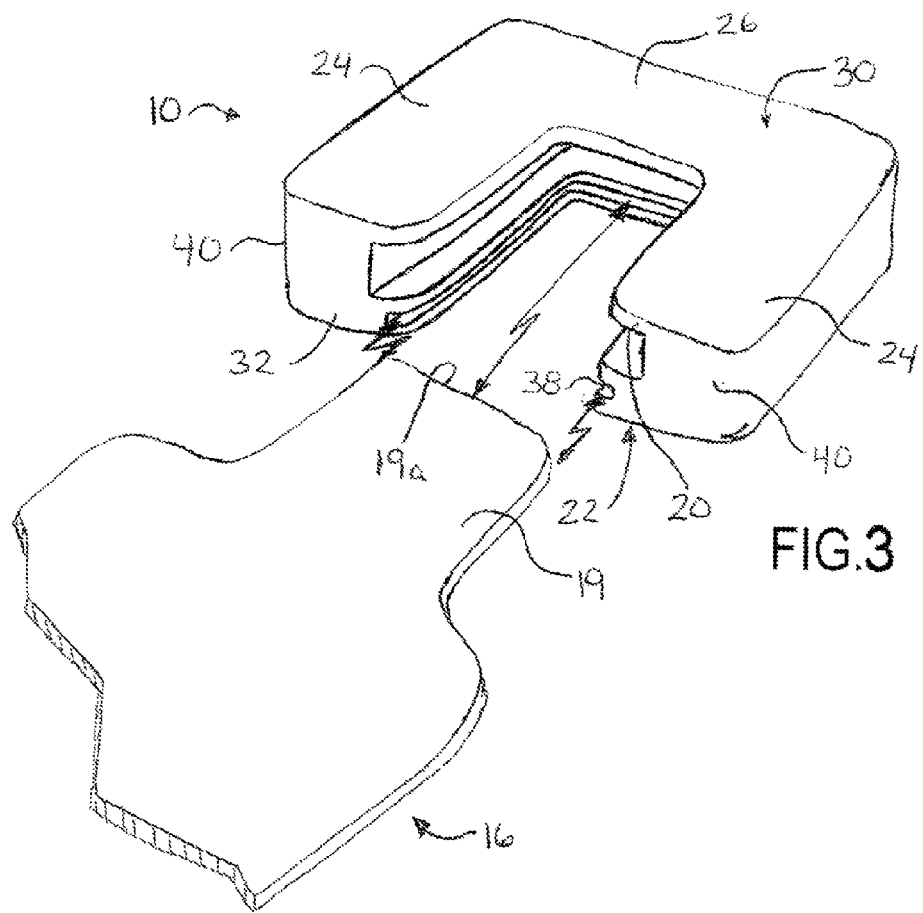
FIG. 3 is an partial exploded view of collar in a pre-mounted relationship with the treatment bed's support plate.

Referring now to FIGs., the present invention is an arm positioning collar 10 suitable for supporting the arms of a pediatric patient in a comfortable position that does not interfere with a catheterization or imaging procedure.

In the illustrated embodiment, the arm positioning collar 10 is an accessory which is used when an individual receiving medical services is too small to safely position their body upon a treatment bed. The collar 10 is mounted to a conventional treatment bed 12 having a mattress 14 supported by a generally flat, rigid support plate 16. In most treatment bed's the support plate 16 is in a cantilevered relationship relative to its base to allow full access above and below the outwardly projecting plate and its mattress 14. As shown, the "upper" end of the mattress 14 and support plate 16 are both narrowed to produce a typical head and shoulder profile 18 and 19, respectively. In the non-limiting embodiment described herein, the collar 10 is sized to mate with a treatment bed 12 with a support plate 16 thickness of approximately one-quarter inch, while the mattress is approximately 3 inches thick.

Figure 4:
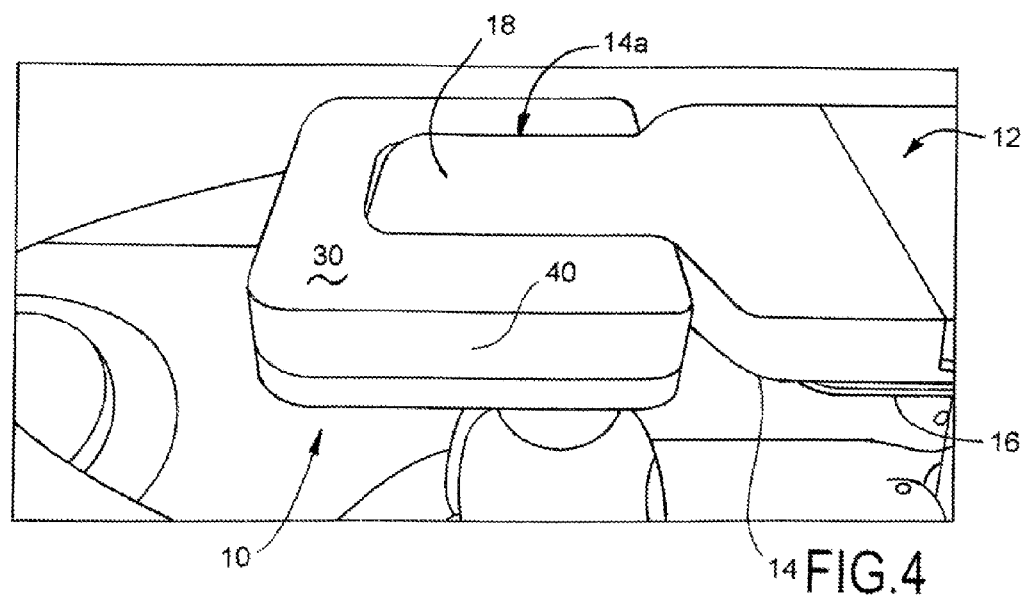
FIG. 4 is a plan view of the collar mounted upon a treatment bed with the mattress nested within the U-shaped collar's central opening.

The collar 10 has a general U-shaped configuration with a planar table 20 fixed upon a bed-mounting structure 22. Two parallel spaced legs 24 are joined together at one end by a bridge portion 26 to cooperatively define a central opening 28. As shown best in FIG. 4, the legs 24 are spaced apart such that opening 28 is complementary in shape to the mattress' profile 18.

Referring now to FIGS. 1 and 2, the table 20 has a planar top surface 30 which is formed from a smooth, readily washable material. The table 20 is preferably rigid in construction and is mounted atop the bed-mounting structure 22.

Bed-mounting structure 22 includes a bottom base 32 having the same U-shaped configuration of as table 20. The inner walls 34, 35, and 36 of base 32 that face opening 28 include a continuous mounting slot 38 that run the length of the leg walls 34, 36 and along the inwardly facing bridge wall 35. The slot 38 is sized to frictionally receive the flat support plate 16 and the head profile portion 19 in particular. As best represented in FIG. 3, the slot 38 and opening 28 are sized complementary to the support plate's head profile portion 19.

The table 20 and bed mounting structure 22 are separated by raised spacers or walls 40 that position the top surface 30 of the collar to be coplanar with the top surface 14a of the mattress when the collar is mounted upon the bed. In this manner, the collar 10 acts to enlarge the working surface of the treatment bed 12.

In operation, when medical personnel determine that the proper protocol is to position a smaller patient's arms overhead during a procedure (e.g., cardiac catheterization), collar 10 is slidably mounted upon the treatment bed 12 with the head profile portion 19 of support plate 16 inserted within slot 38 until the forward edge 19a is located within the bridge portion 38a of the slot. The head portion of the mattress 14 is received within opening 28 with the complementary shapes of the opening 28 and mattress portion 18 presenting only a small gap between the adjoining surfaces. The patient can then be placed upon the treatment bed with the collar 10 surrounding the patient's head (and possibly upper body). When the patient's arms are positioned overhead, the collar 10 provides additional surface to safely support the patient, while providing additional work surface for the medical personnel.

It should be appreciated that the smooth top surface 30 permits the medical staff to apply and remove medical tape to the collar 10 to hold materials and/or the patient's arms in a desired position (e.g., overhead).

From the foregoing description, one skilled in the art will readily recognize that the present invention is directed to an improved system and method for supporting a pediatric patient's upper body and arms in particular upon an adult-sized treatment bed. While the present invention has been described with particular reference to various preferred embodiments, one skilled in the art will recognize from the foregoing discussion and accompanying drawing that changes, modifications and variations can be made in the present invention without departing from the spirit and scope thereof.

For example and without limitation, in other embodiments the table 20 and mounting structure 22 may be adjustable to alter the size and/or shape of opening 28 to accommodate various bed sizes or shapes. Further the distance and relative angle between the top surface 30 and the mounting structure's slot 38 may be changed to accommodate different mattress thicknesses and/or permitting the table 20 to pivot relative to the mounting structure.

The invention claimed is:

1. A collar for use with a medical treatment table having a mattress atop a planar rigid support plate, comprising:
   a pair of parallel spaced legs joined together at one end by a bridge portion, the legs and bridge create a U-shape and cooperate to define a central opening, wherein inwardly facing walls of said legs and bridge include a continuous mounting groove which is complementary to said support plate; and
   a planar table top surface which covers said legs and bridge and which is coplanar with a top surface of said mattress when said plate is inserted within said groove, wherein said central opening receives a portion of said mattress;
   wherein said collar is removably supported by said rigid support plate when said plate is inserted within said groove.

2. A collar as defined in claim 1, wherein said support plate and said mattress each have a body portion of a certain width and a head portion at one end, wherein said support plate and mattress both narrow at said head portion to form a head profile, wherein said central opening is complementary to said mattress head profile and said mounting groove is complementary to said support plate head profile.

3. A collar as defined in claim 2, wherein said table top over said legs has a width matching the certain width of said mattress body portion.

4. A collar for enlarging a work surface upon a medical treatment bed having a mattress supported at one end by a cantilevered rigid planar plate, comprising:
   a bed-mounting structure having two spaced parallel legs joined at one end by a bridge, inwardly facing walls of said legs and bridge cooperate to define a central opening, a continuous mounting groove is formed into the inwardly facing walls; and
   a smooth U-shaped planar table top mounted atop said bed-mounting structure, said table top having an enlarged opening;
   wherein said continuous mounting groove is sized to receive an end of said cantilevered plate to removably couple said collar to said medical treatment bed;
   wherein said table top surround one end of said mattress when said plate is inserted within said continuous mounting groove;
   wherein said cantilevered plate and said mattress each have a body portion of a certain width and a head portion at one end, wherein said cantilevered plate and mattress both narrow at said head portion to form a head profile, wherein said enlarged opening is complementary to said mattress head profile and said mounting groove is complementary to said cantilevered plate head profile.

5. A collar as defined in claim 4, wherein said table top over said legs has a width matching the certain width of said mattress body portion.

6. A method of increasing the work space available on a medical treatment bed having a mattress supported at one end by a cantilevered rigid planar plate, comprising the steps of:
   providing a mounting structure having two spaced parallel legs joined at one end by a bridge, inwardly facing walls of said legs and bridge cooperate to define a central opening, a continuous mounting groove is formed into the inwardly facing walls; providing a U-shaped planar table top mounted atop said mounting structure;
   coupling said mounting structure to said bed by inserting said cantilevered plate into said mounting groove, wherein one end of said mattress is received within said central opening; and
   spacing said a table top from said bed-mounting structure, whereby a top surface of said table top is coplanar with a top surface of said mattress.

7. The method of claim 6, wherein said cantilevered plate and said mattress each have a body portion of a certain width and a head portion at one end, wherein said cantilevered plate and mattress both narrow at said head portion to form a head profile, further comprising the step of:
   matching the width of said table top to said certain width of said mattress.

* * * * *